US010357533B2

(12) United States Patent
Kosorukov et al.

(10) Patent No.: US 10,357,533 B2
(45) Date of Patent: Jul. 23, 2019

(54) DRUG FOR THE EFFECTIVE CONTROL OF ACUTE AND OR CHRONIC PAIN AND A METHOD FOR ITS ADMINISTRATION

(71) Applicant: PVP LABS PTE. LTD., Singapore (SG)

(72) Inventors: Vyacheslav Stanislavovich Kosorukov, Gorki Leninsky (RU); Evgeny Stanislavovic Rzhaninov, Moscow (RU); Nikolai Vasilievich Korobov, Moscow (RU)

(73) Assignee: PVP LaBs PTE, Ltd., Singapore (SG)

( * ) Notice: Subject to any disclaimer, the term of this patent is extended or adjusted under 35 U.S.C. 154(b) by 0 days.

(21) Appl. No.: 15/755,362

(22) PCT Filed: Apr. 13, 2017

(86) PCT No.: PCT/SG2017/050210
§ 371 (c)(1),
(2) Date: May 8, 2018

(87) PCT Pub. No.: WO2017/180064
PCT Pub. Date: Oct. 19, 2017

(65) Prior Publication Data
US 2018/0221432 A1     Aug. 9, 2018

(30) Foreign Application Priority Data

Apr. 14, 2016  (SG) .......................... 10201602973W
Aug. 12, 2016  (RU) ............................... 2016133329

(51) Int. Cl.
| A61K 38/07 | (2006.01) |
| A61P 29/00 | (2006.01) |
| A61K 9/00 | (2006.01) |
| A61K 9/16 | (2006.01) |
| A61K 47/02 | (2006.01) |
| A61K 47/10 | (2017.01) |
| A61K 47/12 | (2006.01) |
| A61K 47/18 | (2017.01) |
| A61K 47/32 | (2006.01) |
| C07K 5/107 | (2006.01) |

(52) U.S. Cl.
CPC ............ *A61K 38/07* (2013.01); *A61K 9/0019* (2013.01); *A61K 9/1611* (2013.01); *A61K 9/1617* (2013.01); *A61K 9/1623* (2013.01); *A61K 9/1635* (2013.01); *A61K 47/02* (2013.01); *A61K 47/10* (2013.01); *A61K 47/12* (2013.01); *A61K 47/183* (2013.01); *A61K 47/32* (2013.01); *A61P 29/00* (2018.01); *C07K 5/1016* (2013.01)

(58) Field of Classification Search
None
See application file for complete search history.

(56) References Cited

U.S. PATENT DOCUMENTS 5,602,100 A * 2/1997 Brown ................. C07K 5/1016
514/18.3

FOREIGN PATENT DOCUMENTS

| JP | S6054400 A | 3/1985 |
| RU | 2538727 | 1/2015 |

OTHER PUBLICATIONS

Sasaki et al., "The Analgesic Activity of D-Arg2-Dermorphin and Its N-terminal Tetrapeptide Analogs After Subcutaneous Administration in Mice", Neuropeptides, 391-394, 1985 (Year: 1985).*
American Physical Therapy Association, "Move Forward Guide: Physical Therapist's Guide to Pain", http://www.apta.org, created 2014; accessed Feb. 7, 2019 (Year: 2014).*
Chaki et al., "Antinociception and physical dependence produced by [D-Arg2] dermorphin tetrapeptide analogues and morphine in rats", Br. J. Pharmacol. (1988), pp. 15-22 (Year: 1988).*
Turner et al.,"Adnninistration of Substances to Laboratory Animals: Equipment Considerations, Vehicle Selection, and Solute Preparation", Journal of the American Association for Laboratory Animal Science, 2011, pp. 614-627 (Year: 2011).*
ICI Americas Inc., "The HLB System: A time-saving guide to emulsifier selection", 1976, pp. 1-22 (Year: 1976).*
Prannanick et al., "Excipient Selection in Parenteral Formulation Development", Pharma Times, Mar. 2013, pp. 65-77 (Year: 2013).*
Rahman et al., "Synergistic Effects of Disintegrants of Release of poorly Water soluble drug", International Journal of Pharmaceutical and Life Sciences, 2012, pp. 1-11 (Year: 2012).*
Chaki, K. et al. Antinociceptive cross-tolerance between [D-Arg2] dermorphin tetrapeptide analogues and morphine. Peptides. Jan.-Feb. 1990; 11(1) pp. 139-144.
Mizoguchi, H. et al. Contribution of spinal m1-opioid receptors and dynorphin B to the antinociception induced by Tyr-D-Arg-Phe-Sar. Peptides. 2006. 27(11): 2786-2793, abstrct.

(Continued)

*Primary Examiner* — Lianko G Garyu

(74) *Attorney, Agent, or Firm* — Aleksandr Smushkovich

(57) ABSTRACT

The proposed drug relates to medicine and veterinary applications, in particular, as a means for effective control of acute and/or chronic pain, and may be used in emergency medicine for the treatment of acute and/or chronic pain, including the late stages of cancer. The stated means is based on a compound for preventing and/or treating acute or chronic pain in a subject, including an analgesic peptide having an amino acid sequence H-Tyr-D-Arg-Phe-Gly-NH2 or an amino acid sequence H-Tyr-D-Arg-Phe-Sar-OH. Also, a method of use/administration of the compound for the prevention and/or treatment of acute and/or chronic pain is disclosed.

18 Claims, No Drawings

(56) References Cited

OTHER PUBLICATIONS

Chaki, K. et al. Antinociception and physical dependence produced by [D-Arg2]—dermorphin tetrapeptide analogues and morphine in rats. Brit.J.Phamacol.1988 95(1):15-22.
Pramanick, S. et al. Excipient selection in parenteral formulation development. Pharma Times. 2013. 45(3): 65-72.
Ogawa T., et al., Synthesis and structure-activity relationships of an orally available and long-acting analgesic peptide, N(alpha)-amidino-Tyr-D-Arg-Phe-MebetaAla-OH (ADAMB), J. Med. Chem., 2002, 5081-5089.
Sato T., et al., Opioid activities of D-Arg2-substituted tetrapeptides. J. Pharmacol Exp Ther. Aug. 1987; 242(2): 654-9.,—abstract.
Sasaki Y., et al., D-Arg2-dermorphin tetrapeptide analogs: a potent and long-lasting analgesic activity atier subcutaneous administration. Biochem. Biophys Res commun, Apr. 1984 214-218.

* cited by examiner

DRUG FOR THE EFFECTIVE CONTROL OF ACUTE AND OR CHRONIC PAIN AND A METHOD FOR ITS ADMINISTRATION

CROSS-REFERENCE TO RELATED APPLICATIONS

This application is a U.S. national stage application of an international application PCT/SG2017/050210 filed on 13 Apr. 2017, published as WO/2017/180064, whose disclosure is incorporated herein in its entirety by reference, which international application claims priority of a Singapore patent application SG10201602973W filed on 14 Apr. 2016 and a Russian Federation patent application RU2016133329 filed on 12 Aug. 2016.

FIELD OF THE INVENTION

The invention relates to medical and veterinary fields of medicine, in particular, as a means for effective control of acute and/or chronic pain. The invention can be used in emergency medicine and the treatment of acute and/or chronic pain, including the late stages of cancer.

BACKGROUND TO THE INVENTION

The following discussion of the background to the invention is intended to facilitate an understanding of the present invention. However, it should be appreciated that the discussion is not an acknowledgment or admission that any of the material referred to was published, known or part of the common general knowledge in any jurisdiction as at the priority date of the application.

Classical approaches in relieving acute pain therapy are presented, based on the search for ligands that interact with opioid receptors (OR) in the human body. There are three major groups of OR: mu (μ-), delta (δ-) and kappa (κ-) receptors. It is believed that those mainly responsible for the analgesic effect are mu-receptors, whereas delta and kappa have different physiological effects: analgesic, euphoric, dysphoric, respiratory depression, etc.

Often in patients with generalized stages of cancer there a combination of several types of pain observed, as are the sources of the pain. Therefore, pain is quite diverse in its clinical manifestations, but it has common characteristics—it is constant, and as a rule, it is also progressive in nature. In some patients, the pain is a result of tumor growth or its' spreading to other organs. In other cases, the pain can occur due to complications from cancer treatment. Approximately 3.5 million patients suffer from daily pain of varying intensity. According to statistics, about 40% of patients with intermediate stages of the disease, and 60-87% of the generalization of the disease experience pain ranging from mild to severe.

In cases of minor or medium manifestations of pain, both periodic and chronic in nature, drugs of the first and second order are used—non-narcotic drugs (non-opioid), non-steroidal anti-inflammatory drugs, or weak opioids (codeine, dionin, Tramal). Non-narcotic analgesics have no effect on the respiratory system, do not cause euphoria or physical and mental dependence. However, their analgesic activity manifests itself mainly with neuralgic, muscle, joint pain, headache, toothache. In cases of severe pain associated with injuries, surgery, malignant tumors and so on, they are commonly ineffective.

Another undesirable side effect of these drugs is the negative effect on the gastrointestinal tract, hematopoietic system and excretory system.

Over time, cancer patients, who have been receiving relatively weak drugs, find that they cease to have a pronounced effect. In such cases, use of opioid-based drugs is prescribed. The group of low-molecular narcotic analgesics (morphine and its derivatives) is characterized by a strong analgesic effect, which allows their use in case of injuries and diseases accompanied by severe pain (cancer, myocardial infarction, etc.). Despite this, this group has a big disadvantage—they have an effect on the central nervous system, which manifests itself in the development of euphoria, and when there is repeated use, of addictive syndromes are observed, as a result of psychic and physical dependence.

It is no secret that just this property allows someone to use them as street drugs and due to this problem, this drug group is under strict control from governments to avoid drug trafficking. Another negative factor is the relatively narrow therapeutic range of administered doses. The risk for adverse effects such as respiratory depression and loss of consciousness, can lead to severe consequences, including death.

The search for new analgesics is a highly topical problem of modern pharmacology as applied to the treatment of pain, primarily because painkillers do not have the necessary balance in efficiency and safety.

The search for peptide based analgesic drugs is an interesting and challenging problem in modern experimental pharmacology. In fact, the essence of natural endogenous peptides of this group of drugs is potentially highly effective and selective for the determination of analgesic and euphoric activities. Features of the chemical structure of several amino acids do not allow a peptide based drug to be chemically modified to induce euphoria.

There are several known studies where various substances have been tested for the presence of peptide based analgesic activity. Among endogenous analgesic peptides there are beta-endorphin, met-enkephalin, leu-enkephalin, dynorphin A. However, the drugs are not convenient to use, due to their biochemical characteristics and large molecules.

In the 1980's, a natural peptide was discovered, that has an affinity for the opioid receptor—dermorphin. Various forms and modifications of dermorphin-derived peptides have been studied.

A known heptapeptide having analgesic activity, combined with thermoregulatory and/or vasomotor activity and/or an impact on the behavioral response of a subject, and the way to change physiological activity of dermorphin [Patent RU No 2134121, was issued Aug. 10, 1999], and has the properties of endogenous analgesics. The use of this peptide provides a change in the level of analgesic activity and thermoregulatory source of dermorphin. However, the analgesic activity level of dermorphin that has been modified in this way, has shown that the activity level is not high enough.

At the same time, according to earlier studies dedicated to this issue, it was found that the minimum requirement for a complete sequence of dermorphin regarding its analgesic activity were represented by N-terminal tetrapeptide in which required the presence of D-Ala-residue [1].

Furthermore, it was shown that D-Arg2-dermorphin and N-terminal tetrapeptide analogs were resistant to cleavage and a peptide has a potent anti-nociceptive effect [2]. It was noted that the tetrapeptide H-Tyr-D-Ala-Phe-Gly-OH was the most resistant to cleavage.

Given the potential importance of this class of tetrapeptides for clinical applications, there were a number of applications filed for inventions JPS58213743 (A), published 12 Dec. 1983 and JPS6054400 (A), published 28 Mar. 1985.

Application JPS58213743 (A) pertaining to the possibility of obtaining tetrapeptides, in particular, H-Tyr-D-Arg-Phe-Gly-$NH_2$ and H-Tyr-D-Arg-Phe-Sar-OH, indicated their potential activity associated with opioid receptors.

Application JPS6054400 indicated on the analgesic activity of tetrapeptides. In particular, given the presence of pronounced analgesic action of tetrapeptide Tyr-D-Arg-Phe-Gly-$NH_2$ (more than 6 times the activity of morphine). This peptide was administered subcutaneously to mice in a condition of acute pain, wherein the solvent used was a ringer solution. In addition, the application describes the potential ability to prepare a composition for administration, without giving any examples of any such compositions.

A certain disadvantage of these tetrapeptides was the presence of some physical dependency and development of a tolerance to them [3]. During long-term administration of tetrapeptide Tyr-D-Arg-Phe-Gly-$NH_2$ it led to the development of a tolerance in mice, to the analgesic effect of the peptide [4]. In another study, it was shown that rats also developed physical dependence, but the signs of addiction were significantly less pronounced than in the development of physical dependence to morphine [5]. This is due to a similar mechanism of action in tetrapeptides and small molecules in morphine-like substances, but significant difference in the manifestations of side effects tells about difference in the mechanism of action.

Most claimed tetrapeptide selectivity to different types of opioid receptors, as well as close to the natural metabolism of biochemical transformations internalized into the cell receptors provides milder effects of tolerance and dependence when used in therapeutic doses.

One of the most important features of the biological activities of the peptides H-Tyr-D-Arg-Phe-Gly-$NH_2$ and H-Tyr-D-Arg-Phe-Sar-OH is the lack of serious side effects, such as effects on the central nervous system in the form of a disturbance of consciousness and the development of euphoria, as well as the lack of effect on the respiratory system.

Another positive feature of the noted tetrapeptides is the wide therapeutic range of application without significant side effects. These features allow the use of drugs based on tetrapeptides in a wider therapeutic range, outside of hospitals, in the field, or at home, which can be administered by low skilled personnel or by the patients' themselves.

SUMMARY OF THE INVENTION

Throughout this document, unless otherwise indicated to the contrary, the terms "comprising", "consisting of", and the like, are to be construed as non-exhaustive, or in other words, as meaning "including, but not limited to".

The present invention is based on an analgesic peptide substance with a structure H-Tyr-D-Arg-Phe-Gly-$NH_2$ and/or H-Tyr-D-Arg-Phe-Sar-OH. This pharmaceutical composition can be recommended to treat chronic pain of cancer patients at the late stages of the disease and is effective in treating acute pain under extreme conditions. This pharmaceutical composition is considered to be a highly effective pain killer when it is used for subcutaneous, intravenous, intradermally, intranasal, skin patches, rectal suppositories or transdermal therapeutic systems to treat chronic pain in patients with cancer at the late stages.

The objective of the present invention is the development of a compound, method, and a means of use of a compound comprising as an active ingredient, one or more selected from tetrapeptides H-Tyr-D-Arg-Phe-Gly-$NH_2$ and H-Tyr-D-Arg-Phe-Sar-OH, which is a highly active analgesic agent for injection, infusion and/or nasal administration for the prevention and/or treatment of acute and/or chronic pain and that can be stored for long periods in the form of a solution and emulsion for direct administration as well as in dry powder form, for example in the form of dry powder or lyophilized form.

The problem is solved in that the proposed means for injecting and/or nasal administration of the tetrapeptide based sequence H-Tyr-D-Arg-Phe-Gly-$NH_2$ and/or H-Tyr-D-Arg-Phe-Sar-OH, for the prevention of, and/or treatment of acute and/or chronic pain, which contains as active ingredient a therapeutically effective amount of the tetrapeptide sequence H-Tyr-D-Arg-Phe-Gly-$NH_2$ and/or H-Tyr-D-Arg-Phe-Sar-OH and at least one auxiliary substance selected from the group consisting of stabilizers, prolongation, buffering additives, emulsifiers/solubilizers, solvents, fillers, preservatives, and other auxiliary substances permitted for medical use. The proposed composition contains preferably the following ratio, in mass percentage (mass %):

Tetrapeptide sequence H-Tyr-D-Arg-Phe-Gly-$NH_2$ and/or H-Tyr-D-Arg-Phe-Sar-OH—0.01-99.99. Excipients to 100.

The stabilizer comprises at least one substance selected from the group consisting of Trilon B, sodium metabisulfite, sodium thiosulfate, glycine, arginine, histidine, lysine or their physiologically acceptable salts, such as hydrochloride, sulfate, acetate, glutamate, aspartate and maleate or other;

The prolongation substance comprises at least one substance selected from the group consisting of polyvinylpyrrolidone having a molecular weight of 10-60 kDa, dextran with a molecular weight of 10-100 kDa, polyvinyl alcohol, glycerol, carboxymethyl cellulose and its salts;

The buffering additive comprises at least one substance selected from the group consisting of sodium chloride, sodium/potassium hydro- and/or dihydrogen phosphate, sodium or ammonium acetate;

The emulsifier/solubilizer comprises at least one substance selected from the group consisting of soy bean lecithin, polysorbate 20, polysorbate 60, polysorbate 80, sorbitan palmitate, Span 20, Span 40, Span 60, Span-85 and sodium dodecyl sulfate;

The solvent comprises at least one substance selected from the group consisting of, water for injection, sterile saline, olive oil, peach kernel oil and sunflower oil;

The filler comprises at least one substance selected from the group consisting of sorbitol, mannitol, xylitol, lactose, sucrose, dextrose, a copolymer of lactic and glycolic acids;

The preservative comprises at least one substance selected from the group consisting chlorobutanol hydrate, ethyl alcohol (ethanol), benzyl alcohol, phenol, cresol, metacresol, chlorocresol, benzoic acid, sorbic acid, merthiolate, nipagin, nipasol, methyl paraben, propyl paraben, benzalkonium chloride or bromide, benzethonium chloride, cetylpyridinium chloride, lauryl dimethyl benzyl ammonium chloride.

The proposed means for administration can be in the form of a dry powder, solution for intramuscular or intravenous administration, subcutaneous or intradermal injection or infusion solution.

The proposed means for nasal administration may be in the form of a dry powder, emulsion, liquid solution.

The proposed agent in a liquid form should have a pH of 4 to 8. Preferably 4.5-5.5.

The invention consists in the fact that, as was experimentally established, the addition to the tetrapeptide sequence H-Tyr-D-Arg-Phe-Gly-NH$_2$ and/or H-Tyr-D-Arg-Phe-Sar-OH of one of the excipients listed above improves biological bioavailability, reduces the development of adverse effects as expressed in the disorders of the central nervous system and respiratory failure, the development of tolerance to treatment, resulting in a more pronounced pharmacological result.

Thus, the developed substance allows its use in medical therapy for the treatment or prevention of acute or chronic pain, facilitates administration of the therapeutic dose required, and ensures the accuracy of amount required for a therapeutic dose.

In addition to the therapeutic advantages listed above, the proposed substance is stable at room temperature, and has a long shelf life (at least 2 years).

We have experimentally selected and studied injectable formulations and/or nasal administration for the prevention and/or treatment of acute and/or chronic pain of various origins containing the following components:

1. Liquid dosage forms for injecting:

|  | Range, mass % |
|---|---|
| Buffer | 0.01-0.2 |
| Filler | 0-6 |
| Stabilizer | 0-4 |
| Tetrapeptide substance | 0.01-5 |
| Solvent | To 100 |

The pH is in the range of 4-8. This form has a shelf life of 2 years at +4-18° C.

2. Powder form (dissolved composition after dilution with water for injection, up to 1 ml):

|  | Range, mass % |
|---|---|
| Buffer | 0.01-0.2 |
| Filler | 0-6 |
| Prolongator | 0-8 |
| Stabilizer | 0-4 |
| Tetrapeptide substance | 0.01-99.99 |

The pH is in the range of 4-8 after dissolution. This form has a shelf life of more than 2 years at +4-18° C.

3. For nasal form, the liquid form is used with the addition of preservatives:

|  | Range, mass % |
|---|---|
| Buffer | 0.01-0.2 |
| Filler | 0-1.5 |
| Stabilizer | 0-1.5 |
| Tetrapeptide substance | 0.01-5 |
| Preservative | 0-0.5 |
| Solvent | To 100 |

The pH is in the range of 4-8.

The compositions can be applied in the following diseases, which are accompanied by pain, acute and/or chronic in nature:
Oncology;
Pain for cancer usually 3-4 stage or in hospice mode;
Burns of various origins;
Traumatic and surgical pain;
Injuries, postoperative analgesic, use in emergency medicine;
Parturition;
Cardiology.

The compositions can be used in myocardial infarction, unstable angina—i.e. the state, accompanied by severe pain. Because heart diseases are among the most common, the need for such analgesic therapy occurs frequently.

In the field of veterinary science, compositions can be used in the operation and use of postoperative analgesia for domestic and farm animals, for the treatment of pain in horses with injuries, sterilization operations and artificial insemination, etc.

In special cases, the substance can be used in the following compounds we developed experimentally. A means for injecting and/or nasal administration for the prevention and/or treatment of acute and/or chronic pain of various origins containing the following components:

1. Liquid Dosage Forms for Injecting:

|  | Range, mass % |
|---|---|
| Sodium acetate | 0.01-0.2 |
| Sodium chlorite | 0-1 |
| Mannitol | 0-6 |
| Glycine | 0-4 |
| Tetrapeptide substance | 0.1-2 |
| Water for injections | To 100 |

The pH is in the range of 4-8. This form has a shelf life of more than 2 years at +4-18° C.

2. Powder form (dissolved composition after dilution with water for injection, up to 1 ml):

|  | Range mass % |
|---|---|
| Sodium acetate | 0.01-0.2 |
| Mannitol | 0-6 |
| Polyvinylpyrrolidone middle MW | 0-8 |
| Glycine | 0-4 |
| Tetrapeptide substance | 0.1-99.99 |

The pH is in the range of 4-8 after dilution. This form has a shelf life of more than 2 years at +4-18° C.

3. For Nasal Form, the Liquid Form is Used with the Addition of Preservatives:

|  | Range, mass % |
|---|---|
| Sodium acetate | 0.01-0.2 |
| Sodium chlorite | 0-1 |
| Mannitol | 0-1.5 |
| Glycine | 0-1.5 |
| Metacresol | 0-0.5 |
| Tetrapeptide | 0.05-2 |
| Water for injection | To 100 |

The pH is in the range of 4-8.

A preparation method is also proposed for a means for injecting and/or nasal administration, based on the sequence of the tetrapeptide H-Tyr-D-Arg-Phe-Gly-NH$_2$ and/or H-Tyr-D-Arg-Phe-Sar-OH, for preventing and/or curing extreme and/or chronic pain, by combining one or more tetrapeptides with the following sequence: H-Tyr-D-Arg-Phe-Gly-NH$_2$ or H-Tyr-D-Arg-Phe-Sar-OH with at least one appropriate excipient and, if necessary, sterilization agents;

pouring the solution into ampoules, vials or containers for infusion solutions; lyophilization; ampoule closing or capping of bottles with the finished product.

Also provided is a method for preventing and/or treating acute and/or chronic pain, comprising administering the above-mentioned substance for injecting and/or by nasal administration of the tetrapeptide sequence H-Tyr-D-Arg-Phe-Gly-NH$_2$ and/or H-Tyr-D-Arg-Phe-Sar-OH in a therapeutic dose.

Depending on the specific features of the clinical case and the patient's physiological parameters, the substance is administered by injection, preferably subcutaneously or intradermally or intra-nasally with a 0.5-10 mg tetrapeptide(s). Before using the powdered form, it is diluted with water for injection in the amount of 1-2 ml, and preferably in the amount of 1.2 ml.

In accordance to a first aspect of the present invention, there is provided a compound for preventing and/or treating acute and/or chronic pain in a subject, comprising an analgesic peptide having an amino acid sequence H-Tyr-D-Arg-Phe-Gly-NH$_2$ or an amino acid sequence H-Tyr-D-Arg-Phe-Sar-OH.

Preferably, the analgesic peptide having the amino acid sequence H-Tyr-D-Arg-Phe-Gly-NH$_2$ or the amino acid sequence H-Tyr-D-Arg-Phe-Sar-OH is present in an amount of 0.01 to 5 mass %.

Preferably, the analgesic peptide having the amino acid sequence H-Tyr-D-Arg-Phe-Gly-NH$_2$ or the amino acid sequence H-Tyr-D-Arg-Phe-Sar-OH is present in an amount of 1 to 5 mass %.

In accordance with a second aspect of the present invention, there is provided a composition comprising an analgesic peptide having an amino acid sequence H-Tyr-D-Arg-Phe-Gly-NH$_2$ or an amino acid sequence H-Tyr-D-Arg-Phe-Sar-OH for preventing and/or treating acute and/or chronic pain in a subject according to the first aspect of the present invention.

Preferably, the composition further comprises at least one excipient, the analgesic peptide and the at least one excipient having the following ratio in mass %: amino acid sequence H-Tyr-D-Arg-Phe-Gly-NH$_2$ or H-Tyr-D-Arg-Phe-Sar-OH—0.01-99.99, excipient to 100.

Preferably, the at least one excipient is selected from the group consisting of: stabilizers, prolongators, buffering additives, emulsifiers/solubilizers, solvents, fillers, preservatives, and other excipients permitted for medical use.

Preferably, the stabilizer comprises at least one substance selected from the group consisting of: Trilon B, sodium metabisulfite, sodium thiosulfate, glycine, arginine, histidine, lysine or their physiologically acceptable salts, such as hydrochloride, sulfate, acetate, glutamate, aspartate and maleate.

Preferably, the prolongator comprises at least one substance selected from the group consisting of: polyvinylpyrrolidone having a molecular weight of 10-60 kDa, dextran with a molecular weight of 10-100 kDa, polyvinyl alcohol and sodium carboxymethyl cellulose.

Preferably, the buffering additive comprises at least one substance selected from the group consisting of: sodium chloride, sodium/potassium hydro- and/or dihydrogen phosphate, sodium acetate and ammonium acetate.

Preferably, the emulsifier/solubilizer comprises at least one substance selected from the group consisting of: soy bean lecithin for injection, polysorbate 20, polysorbate 60, polysorbate 80, Span 20, span-40, span-60, span-85 and sodium dodecyl sulfate.

Preferably, the solvent comprises at least one substance selected from the group consisting of: water for injection, sterile saline, olive oil, peach kernel oil and sunflower oil.

Preferably, the filler comprises at least one substance selected from the group consisting of: sorbitol, mannitol, xylitol, lactose, sucrose, dextrose, a copolymer of lactic and glycolic acids.

Preferably, the preservative comprises at least one substance selected from the group consisting of: chlorobutanol hydrate, ethyl alcohol (ethanol), benzyl alcohol, phenol, cresol, metacresol, chlorocresol, benzoic acid, sorbic acid, merthiolate, nipagin, nipasol, methyl paraben, propyl paraben, benzalkonium chloride or bromide, benzethonium chloride, cetylpyridinium chloride and lauryl dimethyl benzyl ammonium chloride.

Preferably, the composition may have any form suitable for injection and/or enteral administration: nasal spray, nasal drops, sublingual or buccal tablets, rectal suppositories and transdermal transport systems.

Preferably, the composition may be in the form of a dry powder, or in liquid form as a solution for intramuscular or intravenous administration, subcutaneous or intradermal injection or infusion solution, or a solution for nasal administration.

Preferably, the composition in liquid form has a pH of from 4 to 8, preferably 4.5-5.5.

Preferably, the liquid dosage form for administration comprises, for injection, in mass % the following:

| | |
|---|---|
| Buffer | 0.01-0.2 |
| Filler | 0-6 |
| Stabilizer | 0-4 |
| Tetrapeptide Substance | 0.01-5 |
| Solvent | Up to 100 |

Preferably, the powder form comprises (dissolved composition after dilution with water for injection up to 1 ml, in mass %):

| | |
|---|---|
| Buffer | 0.01-0.2 |
| Filler | 0-6 |
| Prolongator | 0-8 |
| Stabilzer | 0-4 |
| Tetrapeptide Substance | 0.01-99.99 |

Preferably, the liquid form for nasal administration comprises in mass % the following:

| | |
|---|---|
| Buffer | 0.01-0.2 |
| Filler | 0-1.5 |
| Stabilizer | 0-1.5 |
| Tetrapeptide Substance | 0.01-5 |
| Preservative | 0-0.5 |
| Solvent | To 100 |

Preferably, the liquid form comprises injecting in mass % the following:
Sodium acetate 0.04
Sodium chlorite 0.5
Mannitol 0.5
Glycine 0.5
Tetrapeptide 0.2
Water for injection to 100
pH to 4.7

Preferably, the powder form contains (dissolved composition after dilution with water for injection up to 1 ml, in mg/ml):

Sodium acetate 0.4 mg
Mannitol 5 mg
Glycine 5 mg
Tetrapeptide 2 mg
pH to 4.7

Preferably, the liquid form for nasal administration preferably contains in mass % the following:

Sodium acetate 0.04
Sodium chlorite 0.5
Mannitol 0.5
Glycine 0.5
Tetrapeptide 0.15
Cresol 0.1
Water for injection to 100 pH to 4.7.

In accordance with a third aspect of the present invention, there is provided a pharmaceutical composition or medicament comprising an analgesic peptide having an amino acid sequence H-Tyr-D-Arg-Phe-Gly-$NH_2$ or an amino acid sequence H-Tyr-D-Arg-Phe-Sar-OH according to any one of the first second aspects of the present invention.

Preferably, the pharmaceutical composition or medicament is for use in a method of medical treatment.

Preferably, the method of medical treatment comprises preventing and/or treating acute and/or chronic pain in a subject.

In accordance with a fourth aspect of the present invention, there is provided a use of an analgesic peptide having an amino acid sequence H-Tyr-D-Arg-Phe-Gly-$NH_2$ or an amino acid sequence H-Tyr-D-Arg-Phe-Sar-OH according to any one of the first and second aspects of the present invention, in the manufacture of a medicament for preventing and/or treating acute and/or chronic pain in a subject.

In accordance with a fifth aspect of the present invention, there is provided an analgesic peptide having an amino acid sequence H-Tyr-D-Arg-Phe-Gly-$NH_2$ or an amino acid sequence H-Tyr-D-Arg-Phe-Sar-OH according to any one of the first and second aspects of the present invention, for use in a method of preventing and/or treating acute and/or chronic pain in a subject, the method comprising administration of a therapeutically effective amount of the analgesic peptide.

Preferably, the analgesic peptide is administered in an amount of 0.01-10 mg/dose, preferably 0.5-10 mg/dose.

In accordance with a sixth aspect of the present invention, there is provided a method of preventing and/or treating acute and/or chronic pain in a subject, comprising a method of administering the compound or composition according to any one of the first and second aspects of the present invention in a therapeutically effective amount.

Preferably, the compound or composition is administered in an amount of 0.01-10 mg/dose, preferably 0.5-10 mg/dose.

Preferably, if a sterilizing agent is necessary; the method further comprises pouring the mixt] In accordance with a seventh aspect of the present invention, there is provided a method of preparation of the composition according to the second aspect of the present invention, comprising mixing the analgesic peptide with at least one suitable excipient.

Preferably, if a sterilizing agent is necessary; the method further comprises pouring the mixture into ampoules, vials or containers for infusion solutions; lyophilization; ampoule closing or capping of vials or containers with the finished product.

Preferably, the at least one excipient is selected from the group consisting of: stabilizers, prolongators, buffering additives, emulsifiers/solubilizers, solvents, fillers, preservatives, and other excipients permitted for medical application.

Preferably, if a stabilizer is used, the stabilizer is selected from the group consisting of: Trilon B, sodium metabisulfite, sodium thiosulfate, glycine, arginine, histidine, lysine or their physiologically acceptable salts, such as hydrochloride, sulfate, acetate, glutamate, aspartate and maleate.

Preferably, if a prolongator is used, the prolongator comprises at least one substance selected from the group consisting of: polyvinylpyrrolidone having a molecular weight of 10-60 kDa, dextran with a molecular weight of 10-100 kDa, polyvinyl alcohol and sodium carboxymethyl cellulose.

Preferably, if a buffering additive is used, the buffering additive comprises at least one substance selected from the group consisting of: sodium chloride, sodium/potassium hydro- and/or dihydrogen phosphate, sodium acetate and ammonium acetate.

Preferably, if emulsifier/solubilizer is used, the emulsifier/solubilizer comprises at least one substance selected from the group consisting of: soy bean lecithin, polysorbate 20, polysorbate 60, polysorbate 80, sorbitan palmitate, Span 20, Span 40, Span 60, Span-85 and sodium dodecyl sulfate.

Preferably, if a solvent is used, the solvent comprises at least one substance selected from the group consisting of: water for injection, sterile saline, olive oil, peach kernel oil and sunflower oil.

Preferably, if a filler is used, the filler comprises at least one substance selected from the group consisting of: sorbitol, mannitol, xylitol, lactose, sucrose, dextrose, a copolymer of lactic and glycolic acids.

Preferably, if a preservative is used, the preservative comprises at least one substance selected from the group consisting of: chlorobutanolum hydratum, ethyl alcohol (ethanol), benzyl alcohol, phenol, cresol, metacresol, chlorocresol, benzoic acid, sorbic acid, merthiolate, nipagin, nipasol, methyl paraben, propyl paraben, benzalkonium chloride or bromide, benzethonium chloride, cetylpyridinium chloride and lauryl dimethyl benzyl ammonium chloride.

Preferably, the preparation may have any form suitable for injection and/or enteral administration: nasal spray, nasal drops, sublingual or buccal tablets, rectal suppositories and transdermal transport systems.

Preferably, the preparation may be in dry powder form, or in liquid form as a solution for intramuscular or intravenous administration, subcutaneous or intradermal injection or infusion solution, or a solution for nasal administration.

Preferably, the preparation in the liquid form has a pH of from 4 to 8, preferably 4.5-5.5.

Other aspects and advantages of the invention will become apparent to those skilled in the art from a review of the ensuing description, which proceeds with reference to the following illustrative drawings of various embodiments of the invention.

DETAILED DESCRIPTION OF THE INVENTION

Particular embodiments of the present invention will now be described. The terminology used herein is for the purpose of describing particular embodiments only and is not intended to limit the scope of the present invention. Additionally, unless defined otherwise, all technical and scientific terms used herein have the same meanings as commonly understood by one of ordinary skill in the art to which this invention belongs.

The use of the singular forms "a", "an", and "the" include both singular and plural referents unless the context clearly indicates otherwise. The use of "or", "/" means "and/or" unless stated otherwise. Furthermore, the use of the terms "including" and "having" as well as other forms of those terms, such as "includes", "included", "has", and "have" are not limiting. The terms "mass %" and "weight %" have the same meaning and can be used interchangeably unless the context clearly indicates otherwise. The term "mass %" or "mass percentage" represents the concentration of an element in a compound or a component in a mixture. Mass percentage is calculated as the mass of a component divided by the total mass of the mixture, multiplied by 100%. For example, a particular substance or component in a liquid mixture has a mass % of 1. This means that one hundred microliters (1000) of the liquid mixture contains 1 mg of the substance or compound. In other words, in one milliliter (1 ml) of the liquid mixture, the substance or compound is present in an amount of 10 mg, i.e. 10 mg/ml. Therefore, 1 mass % equates to 10 mg/ml. The term "excipient" or "excipients" can respectively be referred to as "auxiliary substance" or "auxiliary substances".

For a better understanding of the invention, the following are examples of how to obtain the proposed dosage forms, and the possible composition and properties of the resulting preparation.

Example 1

Obtaining the Peptide

Peptides H-Tyr-D-Arg-Phe-Gly-NH$_2$ and H-Tyr-D-Arg-Phe-Sar-OH, they were synthesized on an automated peptide synthesizer Aapptec Focus XC III solid phase method by Fmoc-protocol on a polymeric support based on Rink polystyrene matrix using DEPCDI/HOBt method amino acid activation. Peptides were cleaved from the resin and unblocked with a mixture of TFA:m-cresol. Purification of the peptide substance was carried by reverse-phase HPLC (column Sigma-Aldrich Co. LLC SUPELCO Ascentis C18 HPLC, 10×250 mm) with a gradient of acetonitrile. The identity of the peptides was determined by examining by mass spectrometry (MALDI). The purity of the product is 98% or better.

Also, peptides can be synthesized by the method described in the applications JPS58213743 (A) and JPS6054400 (A) or any other methods of peptide synthesis in liquid phase or on a solid media.

Example 2

Preparation of Formulation Comprising the Peptide

The basis for the effective preparation, in addition to the active substance, is the formulation of the required dosage. Proper selection of the components of the dosage, maintains the biological effect of the active ingredients of the drug for a long period of time. For the dosage compound that provides long-term preservation of the biological properties of the active peptide, the following composition was developed—1 ml solution: 0.4 mg of sodium acetate, sodium chloride 1.8 mg, 10 mg mannitol, 40 mg polyvinylpyrrolidone 40000, glycine 20 mg, 1.5-3 mg of the tetrapeptide, pH=4.5-5.5 before lyophilization. That provides long-term preservation of the biological properties of the active peptide. The preparation is poured into vials and lyophilized.

After lyophilization, and capping the vials, the residual moisture was tested, which was in the range of 3-4.3% under selected lyophilization conditions.

The composition of the peptide formulation retains its biological activity and stability, when stored at room temperature for a year or more. Preferably, the composition is stored in a dark place at a temperature between 6-10° C.

Example 3

Preparation of a Dry Sterile Powder for Injection

To obtain stable injectable dosage forms of tetrapeptides in a sequence of H-Tyr-D-Arg-Phe-Gly-NH$_2$ or H-Tyr-D-Arg-Phe-Sar-OH in dry powder form, aseptically prepared from sterile trituration tetra peptide and excipients. As a filler in the composition for preparing of dry powder form can be used the above listed sorbitol, mannitol, xylitol, lactose, sucrose, dextrose, a copolymer of D, L-lactic and glycolic acids; substances which have a stabilizing effect on the tetrapeptide molecule (glycine, arginine, histidine, lysine or their physiologically acceptable salts), and other additions are permitted for medical applications.

The specific pharmaceutical composition was produced in a solid sterile form as a dry powder. The drug, in appearance, is an amorphous powder or porous mass of white to yellowish white or yellow color, in an ampoule or vial.

The vial or ampoule contains the following composition after dilution with water for injections to 1 ml (mg/ml):
Sodium acetate 0.4 mg
Mannitol 5 mg
Glycine 5 mg
Tetrapeptide 1.5 mg
pH to 4.7

As stated above, when using ampoules or vial contents were dissolved in 1.2 ml of water for injection. This form has a shelf life of more than 2 years at +4-18° C.

Example 4

Preparation of a Dry Sterile Powder for Injection in Accordance with Another Embodiment Stable injectable dosage forms of tetrapeptides in a sequence of H-Tyr-D-Arg-Phe-Gly-NH$_2$ or H-Tyr-D-Arg-Phe-Sar-OH in dry powder form is prepared as described in Example 3 above. In this particular embodiment, the vial or ampoule contains the following composition after dilution with water for injections to 1 ml (mg/ml):
Sodium acetate 0.4 mg
Mannitol 5 mg
Glycine 5 mg
Tetrapeptide 2 mg
pH to 4.7

As stated above, when using ampoules or vial contents were dissolved in 1.2 ml of water for injection. This form has a shelf life of more than 2 years at +4-18° C.

Example 5

Preparation of an Aqueous Injectable Solution

To prepare a stable injectable solution in water for injection it is first dissolved excipients of prolongation groups/prolongators, stabilizers, etc. For prolongation during the composition stage in an aqueous solution for injection, polyvinylpyrrolidone can be used, with a molecular weight 10-60 kDa, dextran with a molecular mass of 10-100 KDa, glycerol, polyvinyl alcohol, sodium carboxymethyl cellulose. As stabilizers in the composition Trilon B, sodium metabisulfite, sodium thiosulfate, glycine, arginine, histidine, lysine or their physiologically acceptable salts (hydrochloride, sulfate, acetate, glutamate, aspartate and maleate) can be used for the aqueous injection solution.

Then, in the resultant solution of excipients dissolve the tetrapeptide substance. The resulting solution was sterilized by membrane filtration under aseptic conditions, passing through a filter with a pore diameter of 0.22 μm, poured into ampoules or vials in an atmosphere of an inert gas, then packed into an ampoule vial, and become finished products.

Specific pharmaceutical composition is made into liquid form, and in appearance is a transparent liquid sealed in vials or ampoules. One ampoule/vial contains tetrapeptide H-Tyr-D-Arg-Phe-Gly-$NH_2$ or H-Tyr-D-Arg-Phe-Sar-OH. The vial or ampoule contains the following composition in mass %:
Sodium acetate 0.04
Sodium chlorite 0.5
Mannitol 0.5
Glycine 0.5
Tetrapeptide 0.15
Water for injection to 100
pH to 4.7
The obtained preparation is ready for immediate injection. This form has a shelf life of 2 years at +4-18° C.

Example 6

Preparation of an Aqueous Injectable Solution in Accordance with Another Embodiment A stable injectable solution in water for injection is prepared as described in Example 5 above. In this particular embodiment, the vial or ampoule contains the following composition in mass %:
Sodium acetate 0.04
Sodium chlorite 0.5
Mannitol 0.5
Glycine 0.5
Tetrapeptide 0.2
Water for injection to 100
pH to 4.7
The obtained preparation is ready for immediate injection. This form has a shelf life of 2 years at +4-18° C.

Example 7

Preparation of Solution for Nasal Administration

To prepare a stable injectable solution in water, it is first dissolved in excipients of prolongation groups, stabilizers, etc. Because the prolongation composition is an in aqueous solution for injection, polyvinylpyrrolidone can be used, with a molecular weight 10-60 kDa, dextran with a molecular mass of 10-100 kDa, glycerol, polyvinyl alcohol, sodium carboxymethyl cellulose. As stabilizers in the composition Trilon B, sodium metabisulfite, sodium thiosulfate, glycine, arginine, histidine, lysine or their physiologically acceptable salts (hydrochloride, sulfate, acetate, glutamate, aspartate and maleate) can be used for the aqueous injection solution. One of the above preservatives may be included to increase the stability of the antimicrobial composition of the drug.

Then, in the resultant solution of excipients the tetrapeptide substance is dissolved. The resulting solution was sterilized by membrane filtration under aseptic conditions, passing through a filter with a pore diameter of 0.22 μm, poured into glass or polymer container in an atmosphere of inert gas. Then the closure of bottles takes place to receive the finished product.

The specific pharmaceutical composition is made into liquid form, and in appearance it is a transparent liquid sealed in vials with a drip or spray nozzle.

The vial or ampoule contains the following composition in mass %:
Sodium acetate 0.04
Sodium chlorite 0.5
Mannitol 0.5
Glycine 0.5
Tetrapeptide 0.15
Cresol 0.1
Water for injection to 100
pH to 4.7
This form has a shelf life of 1 year at +4-8° C.

Example 8

Preparation of a Lyophilized Powder for Injection

In order to produce a stable, soluble lyophilized powder, with a long shelf life, excipients are used from the groups of fillers, stabilizers, buffering additives and prolongators to produce a solution suitable for injection.

Pharmaceutical composition based tetrapeptides can be prepared by any lyophilization method known. One such method comprises the following steps:
1. Preparation of filling solution.
   Dissolution of the indicated tetrapeptide in water for injection.
   Adding auxiliary substances.
2. Sterilizing filtration, which includes a preliminary filtering and sterilizing filters set in series with a pore diameter of 0.5 and 0.22 μm.
3. Aseptic filling solution in vials or ampoules.
4. Freeze Drying the solution in a freeze-drying installation. Cassettes placed into a freeze-drying device where the solution is and frozen over a period of 4 hours to a temperature (−45°) C. Drying is carried out at a residual pressure of 100 to 120 microns Hg. for 48 hours.
5. Sealing ampoules, capping and crimping of vials to make the finished product.
6. Packaging and labeling.

The pharmaceutical composition is made in the form of a sterile solid, and in appearance is an amorphous powder or friable tablet in an ampoule or vial.

The vial or ampoule contains the following composition, to 1 ml after dilution with water for injection (in mg/ml):
Sodium acetate 0.4 mg
Mannitol 5 mg
Glycine 5 mg
Tetrapeptide 1.5 mg
pH to 4.7
As stated above when using ampoules or vials, the contents were dissolved in 1.2 ml of water for injection.

Example 9

Preparation of a Lyophilized Powder for Injection in Accordance with Another Embodiment.

A stable, soluble lyophilized powder for injection is prepared as described in Example 8 above. In this particular embodiment, the vial or ampoule contains the following composition, to 1 ml after dilution with water for injection (in mg/ml):
Sodium acetate 0.4 mg
Mannitol 5 mg
Glycine 5 mg Tetrapeptide 2 mg
pH to 4.7

As stated above when using ampoules or vials, the contents were dissolved in 1.2 ml of water for injection.

Example 10

Preparation of Tetrapeptide Formulation for Injection Pen Cartridges and Pre-Filled Syringes and Accelerated Storage Testing.

The dosage form is intended for pre-filled syringe or cartridges for injection pen. In this case, the patient is injected subcutaneously with small amounts of the formulation for several times a day.

This dosage form requires the use of a concentrated formulation of tetrapeptide for repeated administration to the patient with a pen injector. In order for the patient to receive the required amount of the drug, its concentration should be significantly higher than with a conventional injection with a syringe. The potential maximum dose for a single administration to a patient may be up to 10 mg peptide. Thus, an injection pen which is capable to administrate a drug of 0.1-0.3 ml should have a cartridge with a tetrapeptide concentration up to 50 mg/ml.

In this example, it was decided to make preparations of peptide formulation for cartridges with a concentration of tetrapeptide 5, 10, 30 and 50 mg/ml.

Specific pharmaceutical compositions are made into liquid form, and in appearance is a transparent liquid packed in cartridges or syringes. One drug unit contains tetrapeptide H-Tyr-D-Arg-Phe-Gly-NH$_2$ or H-Tyr-D-Arg-Phe-Sar-OH.

The cartridge contains the following composition in mass %:

Sodium acetate 0.04
Sodium chlorite 0.2
Mannitol 0.2
Metacresol 0.2
Glycine 0.2
Tetrapeptide 0.5, 1, 3 or 5
Water for injection to 100
pH to 5.2

The resulting solution was sterilized by membrane filtration under aseptic conditions, passing through a filter with a pore diameter of 0.22 μm, poured into cartridges or syringes in an atmosphere of an inert gas and become finished products.

The dosage forms were tested for stability by the method of accelerated storage at temperature 25° C. according to approved methods (ICH harmonized guideline for stability testing of new drug substances and products Q1A(R2)).

TABLE 1

The stability of tetrapeptide formulations in accelerated storage testing at 25° C.

| Time of storage | Tetrapeptide concentration, mg/ml | | | |
|---|---|---|---|---|
| At production | 4.96 | 9.92 | 30.01 | 50.21 |
| 3 month | 4.92 | 9.9 | 29.86 | 49.83 |
| 6 month | 4.92 | 9.76 | 29.65 | 49.39 |
| % of loss at 6 month | 98.0 | 97.3 | 98.5 | 98.0 |

Current storage conditions make it possible to extrapolate the stability of the formulation during storage for 2 years at a temperature of 8-10° C. The loss of active substance in experimental samples was about 2%. The obtained data showed that the tested dosage forms have good stability sufficient for a pharmaceutical preparation.

Example 11

The Effect of the Developed Substance on Peripheral Opioid Activity Based on the Example of the Tetrapeptides H-Tyr-D-Arg-Phe-Gly-NH$_2$ and H-Tyr-D-Arg-Phe-Sar-OH In Vitro.

Effect was assessed by ability to inhibit the contraction caused by electrical stimulation of isolated organs—guinea pig ileum (GPI). Work was carried out on a special apparatus for testing substances for opioid activity on the model of guinea pig ileum. GPI, taken from nonlinear animals were placed in a 10 ml volumetric flask with electrodes inserted containing Krebs solution at 34° C. in a water bath (HOECHST Organbad, Germany) with a thermostat for maintaining a constant temperature in the working cell. The lower end of the GPI is fixed to the vessel at the bottom. The upper end of the ligature was attached to the sensor strength registration device (sensors isometric registration K-30, "Hugo Sachs Elektronik KG", Germany). The initial tension of the organs was 1 gram. The solution with placed in GPI was being constantly aerated. GPI segments were equilibrated in the Krebs solution for one hour.

GPI contractions were stimulated by plate electrodes with electrical impulses in a series of four rectangular pulses each lasting 0.5 ms and with 1.5 ms intervals, with delays at 7.5 sec. between the series and voltage 80V using a generator of electric impulses (type 215/I, Hugo Sachs Elektronik, Germany). Registration was performed in isometric contraction mode using K30 sensors via two channel amplifiers MS 6601 ("Watanabe", Japan).

At the beginning stimulation was applied for a minimum of 45 minutes, which allowed reproducible responses to be established.

The tested substance was administered in a solution bathing the organs in a volume of 0.005 to 0.015 ml, to final concentrations of $1 \times 10^{-9}$-$1 \times 10^{-6}$ M. Each subsequent introduction of the substance was done 1 minute after the previous dose without washing the organs, on a cumulative basis. Based on these data, graphs were built on a dose-response for morphine, and the tested agent. Active substances were expressed on an indicator pD2 (numerically equal to the negative decimal logarithm of the concentration of a substance that causes 50% of the maximum effect). In other words, the potency of the opioid receptor agonists in the absence and presence of the antagonist was assessed as the negative logarithm of the concentration required to cause 50% of the maximum response (pD2) using the logistic equation described by DeLean A. et al [6].

In particular, the characteristics of the opioid peptide activity were evaluated in comparison with a standard solution of morphine. During the experiment, the change in GPI amplitude contractions was taken into account and was fixed. Parallel monitoring in 4 chambers with GPI segments for each substance was used.

The inhibitory effect of morphine and tetrapeptide substance caused by electrical stimulation was prevented by addition of the opioid receptor antagonist naloxone washing solution at a concentration of $10^{-6}$M.

According to the data in Table 2, EC$_{50}$ for morphine was $3.26 \times 10^{-7}$ M, and indicator pD2—6.48. For tetrapeptide substance, EC$_{50}$ was $2.37 \times 10^{-7}$ M, a pD2—6.62. Thus, the activity of the tetrapeptide substance was higher than morphine, exceeding in efficacy and activity, when the drug was applied to the opioid μ-receptors located on GPI.

TABLE 2

The dependence of the degree of suppression of the amplitude of movements GPI depending on the concentration of H-Tyr-D-Arg-Phe-Gly-NH2 (TP1), H-Tyr-D-Arg-Phe-Sar-OH (TP2) or morphine.

| Concen- | Peptide TP1 | | Peptide TP2 | | Morphine | |
|---|---|---|---|---|---|---|
| tration, M | ampli-tude, MM | inhibit. effect, % | ampli-tude, MM | inhibit. effect, % | ampli-tude, MM | inhibit. effect, % |
| 0.0E+00 | 38.7 | 0.0 | 38.2 | 0.0 | 39.5 | 0.0 |
| 1.0E−09 | 38.7 | 0.0 | 38.2 | 0.0 | 39.5 | 0.0 |
| 4.0E−09 | 38.7 | 0.0 | 38.2 | 0.0 | 39.5 | 0.0 |
| 1.4E−08 | 36.0 | 7.0 | 35.3 | 7.6 | 36.0 | 8.7 |
| 4.4E−08 | 30.3 | 22.9 | 29.7 | 22.2 | 29.0 | 25.8 |
| 1.4E−07 | 23.0 | 41.1 | 22.0 | 42.4 | 23.8 | 39.2 |
| 4.4E−07 | 15.7 | 61.1 | 15.2 | 60.2 | 18.0 | 55.0 |
| 1.4E−06 | 9.3 | 76.6 | 8.6 | 77.5 | 13.0 | 68.2 |

The inhibitory effect of morphine and the tetrapeptide substance on GPI contractions caused by electrical stimulation was successfully neutralized by adding into washing solution an opioid receptor antagonist naloxone in concentrations $10^{-6}$M.

Example 12

The Study of the Dose-Dependent Analgesic Effect of the Peptide Compound (in Injection Form as in Example 5 or 6 Based on the Tetrapeptide H-Tyr-D-Arg-Phe-Gly-NH$_2$) in the "Tail Flick" Test in Mice.

This stage involved selecting the effective doses of peptide compound in the tail flick test in mice after a single subcutaneous administration of the substance at doses of 0.01, 0.05, 0.1, 0.5, 0.7, 1 and 5 mg/kg. Tail flick method is based on a spinal flexion reflex in response to a progressively increasing effect of thermal radiation on the surface of skin. A pain stimulus was applied to the tail locally, by the action of thermal radiation, using a TSE Systems analgesiometer (Germany). Stimulus intensity was set, corresponding to an increase in temperature from 30° C. to 60° C. over 13 seconds. The tail flick latency (TFL) of 13 seconds was used as the maximum allowable time of stimulation. The mice in test groups were given peptide compound, and control group mice were given the solvent (water for injections) by subcutaneous. Tail flick latency was evaluated 40 minutes after the administration of the study substance or solvent. The analysis of experimental results involved calculating the maximum possible effect (MPE).

TABLE 3

Effect of Peptide compound administrated by subcutaneous injection on tail flick latency in mice.

| Group | TFL, s (Mean ± SEM) | Proportion of the maximum possible effect (MPE), % |
|---|---|---|
| Control | 4.25 ± 0.54 | — |
| Peptide compound 0.01 mg/kg | 5.89 ± 0.19 | 18.7 |
| Peptide compound 0.05 mg/kg | 7.97 ± 0.78 | 42.5 |
| Peptide compound 0.1 mg/kg | 8.36 ± 0.68 | 47.0 |
| Peptide compound 0.5 mg/kg | 9.12 ± 0.92 | 55.7 |
| Peptide compound 0.7 mg/kg | 10.15 ± 0.74 | 57.5 |
| Peptide compound 1 mg/kg | 12.53 ± 0.24 | 94.6 |
| Peptide compound 5 mg/kg | 13.00 ± 0 | 100 |

According to published data for morphine it has in mice antinociceptive activity 50% of MPE in dosage 7 mg/kg, 75% of MPE in dosage 10 mg/kg and 95% of MPE in dosage 20 mg/kg [7]. During this study, we show that in peptide compound 0.1 mg/kg dose it had the activity close to that of 4 mg/kg of morphine, in 0.5 mg/kg dose had the activity close to that for morphine in 7-8 mg/kg dose and the effect of full analgesia was observed in dose of 1 mg/kg. The work conducted confirmed the significant higher level of peptide compound activity in comparison with morphine approximately by 10-15 times.

Example 13

The Study of the Dose-Dependent Analgesic Effect of the Peptide Compound (in Injection Form as in Example 5 or 6 Based on the Tetrapeptide H-Tyr-D-Arg-Phe-Gly-NH$_2$) in the "Hot Plate" Test in Rats.

The "Hot Plate" test is based on the reflex that rat licking its' feet when the animal comes in contact with a hot surface. The device is a metal surface with a diameter of 30 cm whose temperature is controlled by software. The site is enclosed by a transparent fence with a height of 40 cm. The temperature of the metal pad was set at exactly 52° C. When placing the animal on the surface, you measure the time until the moment when the animal licks its' foot. When analgesics are administered, the time before the rat licks its' feet increases. The licking latency (HPL) of 40 seconds was used as the maximum allowable time of stimulation. The study was conducted on male rats weighing 160-180 g, 6 animals per dose.

TABLE 4

Effect of peptide compound administrated by subcutaneous injection on Hot plate test in rats.

| Group | HPL, s (Mean ± SEM) | Proportion of the maximum possible effect (MPE), % |
|---|---|---|
| Water | 17.35 ± 4.97 | — |
| Peptide compound 0.1 mg/kg | 26.01 ± 8.8 | 38.2 |
| Peptide compound 5 mg/kg | 39.33 ± 1.63 | 98.3 |
| Morphine 5 mg/kg | 27.45 ± 4.4 | 68.6 |
| Morphine 15 mg/kg | 38.31 ± 2.63 | 95.7 |

Studies have shown the presence of high analgesic activity of the invented substance, as compared with control animals receiving placebo or morphine. The effect full analgesia was observed with a peptide analgesic dose of 5 mg/kg. Analgesic efficacy of the proposed drug in a dose of 0.1 mg/kg corresponds, to that of 5 mg/kg of morphine. The conducted work confirmed the data of a significant higher level of peptide compound activity in comparison with morphine approximately by 10 times.

Example 14

Evaluation of the Analgesic Effect of Peptide Compound in the Acetic Acid-Induced Writhing Test in Mice.

The analgesic effect of peptide compound at the three doses (0.25 mg/kg, 0.5 mg/kg and 1 mg/kg) was evaluated in the acetic acid-induced writhing test, a visceral pain test in mice, relative to Morphine. The acetic acid-induced writhing test is a model of a chemical nociceptive stimulus applied by the intraperitoneal injection of acetic acid solution.

Intraperitoneal injection of substances that irritate serous membranes in mice induces distinctive movements, including contractions of abdominal muscles followed by muscle relaxation, extension of the hind limbs and curving of the back, known as writhing. Mice were given an intraperitoneal injection of 1% acetic acid at a dose of 0.1 mL per 10 g body weight. After the injection the mice were placed in transparent acrylic chambers and counted the number of writhings in each animal for the next 15 minutes. The analgesic effect was evaluated by a reduction in the number of writhings in mice that received the study drug relative to the control group. Peptide compound at doses of 0.25 mg/kg, 0.5 mg/kg and 1 mg/kg, the comparator drug Morphine at doses of 1 mg/kg and 3 mg/kg and the vehicle (given to the control group) were administered subcutaneously 40 minutes before the intraperitoneal administration of acetic acid solution. Writhing onset latency in mice was used as an additional parameter for evaluating the efficacy of the substance in the acetic acid-induced writhing test. For animals exhibiting no pain reaction (writhing) throughout the observation period (15 min), writhing onset latency was assumed to be 900 seconds (15 min).

The peptide compound exhibited a dose-dependent analgesic activity. At 0.25 mg/kg, the drug significantly reduced visceral pain by a factor of 2.2 relative to the control group; at 0.5 mg/kg and 1 mg/kg the reduction was by a factor of 31.8 and 74.2 respectively ($p<0.01$). The pronounced effect of peptide compound administered to mice at 0.5 mg/kg and 1 mg/kg is due to the fact that the pain response (writhing) was not observed in all animals in these groups. Specifically, 100% of animals exhibited writhing in the group that received Peptide compound subcutaneously at 0.25 mg/kg, as in the control group; by contrast, at 0.5 mg/kg and 1 mg/kg of the test drug, the pain response was observed in 40.0% (4 of 10 animals in the group) and 55.6% (5 of 9 animals in the group) respectively (Table 3).

Peptide compound was demonstrated to increase writhing onset latency in mice in a dose-dependent manner. Whereas at 0.25 mg/kg writhing onset latency significantly increased by a factor of 2.6 relative to the control group, administration at doses of 0.5 mg/kg and 1 mg/kg produced an increase in writhing onset latency by a factor of 4.1 and 4.9 respectively (Table 3).

The analgesic activity of Peptide compound at 0.5 mg/kg and 1 mg/kg was comparable to that of Morphine, the comparator drug, at 3 mg/kg. The comparator drug at 3 mg/kg significantly reduced the number of writhings by a factor of 42.4 relative to the control group. Absence of the pain response (writhing) occurred in 37.5% (3/8) of mice in this group.

TABLE 5

Effect of peptide compound and Morphine administrated by subcutaneous injection on the degree of pain response in the acetic acid-induced writhing test in mice.

| Group | Number of writhings, n (Mean ± SEM) | Number of mice w/o writhing/number of mice in group (% of mice w/o writhing) | Writhing onset latency, s (Mean ± SEM) |
|---|---|---|---|
| Control | 89.0 ± 2.27 | 0/7 (0%) | 154.3 ± 13.33 |
| Morphine, 1 mg/kg | 12.4 ± 3.73 | 1/7 (14.3%) | 467.1 ± 74.41 |
| Morphine, 3 mg/kg | 2.1 ± 0.83 | 3/8 (37.5%) | 695.0 ± 85.00 |
| Peptide compound 0.25 mg/kg | 40.7 ± 4.50 | 0/9 (0%) | 397.2 ± 69.95 |
| Peptide compound 0.5 mg/kg | 2.8 ± 1.00 | 4/10 (40.0%) | 632.5 ± 80.62 |
| Peptide compound 1 mg/kg | 1.2 ± 0.49 | 5/9 (55.6%)# | 762.8 ± 55.76 |

Therefore, the results of the test to evaluate the effect of peptide compound on the degree of visceral pain (the acetic acid-induced writhing test) confirmed the dose-dependent analgesic activity of the drug at 1 mg/kg and 0.5 mg/kg, which was comparable to the effect of Morphine at 3 mg/kg and exceeded the effect of Morphine at 1 mg/kg.

Example 15

The Duration of Analgesic Effect of Peptide Compound.

The duration of analgesic effect of peptide compound was evaluated in the tail flick test in mice as described above.

Peptide compound was administered to mice subcutaneously at a doses of 0.5 mg/kg, 1.5 mg/kg and 4.5 mg/kg. The control group of animals was given a subcutaneous injection of the vehicle (water for injections). TFL test was evaluated in mice that received peptide compound at 30 minutes and at 1, 2, 4, 6, and 8 hours after dosing.

TABLE 6

Evaluation of the duration of the analgesic effect of peptide compound in the tail flick test, MPE, % (Mean ± SEM).

| Group | Level of TFL after time from subcutaneous injection, hours | | | | | |
|---|---|---|---|---|---|---|
| | 0.5 | 1 | 2 | 4 | 6 | 8 |
| Peptide compound 0.5 mg/kg | 45.6 ± 13.31 | 49.9 ± 11.54 | 15.5 ± 4.78 | 6.3 ± 2.43 | 6.3 ± 2.94 | −2.6 ± 3.18 |
| Peptide compound 1.5 mg/kg | 97.2 ± 2.78 | 62.7 ± 14.4 | 33.4 ± 4.85 | 25.6 ± 11.69 | 4.6 ± 7.8 | 5.3 ± 3.46 |
| Peptide compound 4.5 mg/kg | 100.0 ± 0.00 | 100.0 ± 0.00 | 100.0 ± 0.00 | 49.9 ± 10.21 | 6.5 ± 5.94 | 2.6 ± 4.0 |

According to published data for morphine it has in mice duration of the analgesic effect in dosage 10 mg/kg, about 2-3 hours [7].

Therefore, test results demonstrate that an increase of the dose of peptide compound from 0.5 mg/kg to 1.5 mg/kg and 4.5 mg/kg is associated with an increase in the degree and duration of its analgesic effect. The maximum duration of the analgesic effect was evaluated at 4 hours and was achieved after dosing with 1.5 mg/kg and 4.5 mg/kg of the substance and this effect is longer than in case of morphine.

Example 16

Evaluation of Peptide Compound Antinociceptive Tolerance and Withdrawal Syndrome in Mice.

The tail flick test was the main method of evaluating peptide compound antinociceptive tolerance and withdrawal syndrome. The test involved evaluating tail flick latency (TFLtest). Baseline tail flick latency TFLbase was evaluated before administering the substances. The test was performed in outbred male mice.

The animals were randomized into 4 groups of 10 animals in each group: Group 1: control—the animals were administered subcutaneous injections of water for injections for 14 days; Group 2: single peptide compound administration group—the animals were administered water for injections for 13 days and peptide compound at a dose of 0.5 mg/kg on day 14 by subcutaneous injection; Group 3: chronic peptide compound administration group—the animals were administered with peptide compound at a dose of 0.5 mg/kg by subcutaneous injection for 14 days; Group 4: withdrawal group—the animals were administered with peptide compound at a dose of 0.5 mg/kg by subcutaneous injection for 14 days, withdrawal test was evaluated after 48 hours.

The last injection of the drug/water to groups 1-3 was administered 40 minutes before the test.

TABLE 7

Effect of peptide compound on pain response in the tail flick test in mice (Mean ± SEM)

| Group | TFL, s Baseline values | TFL, s After dosing | MPE, % |
|---|---|---|---|
| 1. Control, water for injections | 4.4 ± 0.26 | 4.7 ± 0.56 | 3.9 ± 4.49 |
| 2. Peptide compound 0.5 mg/kg, single dose | 4.5 ± 0.36 | 8.0 ± 1.03* | 43.3 ± 11.19* |
| 3. Peptide compound 0.5 mg/kg, chronic dosing | 4.6 ± 0.26 | 8.6 ± 1.25# | 50.5 ± 13.92* |
| 4. Peptide compound 0.5 mg/kg, withdrawal | 4.7 ± 0.24 | 4.8 ± 0.36 | 1.3 ± 3.72 |

No analgesic activity or increased pain sensitivity was observed in the group of mice tested after 48 hours of peptide compound withdrawal following 13 days of daily injections: TFL before treatment with Peptide compound and after withdrawal of the drug did not differ (Table 6).

Therefore, this study indicates a pronounced antinociceptive effect of tetrapeptide compound at 0.5 mg/kg (subcutaneously) after a single dosing or chronic treatment, and suggests a lack of tolerance or withdrawal syndrome.

Example 17

Evaluation of the Influence of Peptide Compound on the Behavior of Mice.

Testing of the influence of the injectable substance based on tetrapeptide (as in example 2) H-Tyr-D-Arg-Phe-Gly-NH$_2$ on the behavior of animals, was provided in the study of the toxicity of high doses of the "open field" test and maintaining balance on a horizontal rod.

The aim of the experiment was to identify an effective dose of the substance that affects the behavior of the animals. It was tested on several animals after administration of different doses of peptide compound.

Studied of dosage and method of administration:
1—control without injection
2—injection of 300 µl of saline (stress control)
3—substance of 0.5 mg/kg (EC$_{50}$ analgesic effect)
4—substance of 1.5 mg/kg
5—substance of 5 mg/kg
6—substance of 10 mg/kg (20 doses EC$_{50}$ analgesic effect) 7—substance of 20 mg/kg (40 doses EC$_{50}$ analgesic effect)
8—substance of 100 mg/kg (200 EC$_{50}$ doses of analgesic effect) 9—morphine of 120 mg/kg (20 doses EC$_{50}$ analgesic effect).

The experimental and control groups of male mice were taken from the same batch, about the same weight (22-24 g).

The substance was injected intraperitoneally in identical weight amounts to laboratory animals in the experimental and control groups, respectively. The substance was dissolved in water for injections, so that the total volume of the injected solution did not exceed 0.5 ml. The measurement was started 15 minutes after injection.

Several groups were organized: without the introduction of the substance, and with the introduction of a solution of morphine or peptide. After 15 from injection we conducted measurement in the following order:

"Open field" Test

Each animal tested was introduced into a round, not brightly lit arena. The surface is divided into square blocks of 10 cm each. We count locomotor activity of the mouse when it crossed the square. The movement of the mouse in the center of the arena and on the periphery, are recorded separately. We registered the number of times the mouse stands on its hind legs "stand" and the number of times the mouse looks into a "burrow"—ie. holes in the floor. Observations were done visually and were simultaneously entered into a computer using a keyboard (semi-automatic registration).

Balancing on a Horizontal Rod Test

Animals were placed on a wooden rod with a diameter of 2 cm and 40 cm long, at a height of not less than 60 cm. Then we recorded the duration maintenance of equilibrium on the rod. We processed the results using single factor dispersal analysis ANOVA.

Our studies have shown that the large doses do not lead to a significant loss of orientation of the animals or reduce their behavioral activity. Even at a dose of 100 mg/kg, the mouse continued to actively move around the field, although with slightly reduced activity (by 20-25% at a dose of 20-100 mg/kg). There was observed a 20-30% reduction in exploratory activity (a measure of "stand-burrow").

Our experiments showed that we did not attain a dosage that caused toxic effects. Even at a dose of 100 mg/kg, the animals continued to move actively, breathing was not inhibited, and heart beats were stable.

It should be noted that the administration of the morphine control substance (20 $EC_{50}$ doses), physical activity becomes significantly reduced by 50-70%.

We did not observe significant differences between the experimental and control groups in the test on maintaining balance on a horizontal rod. The experimental animals were well balanced on the shaft. Some difference in the experimental group from the control animals should be noted. It was observed the reduced activity in horizontal movement on the rod (10-20%) after administration of higher doses 20-100 mg/kg.

We concluded that the substance at the proposed dosage does not significantly affect behavioral characteristics of the animals. The use of the substance at doses of up to 200 $EC_{50}$ does not result in toxic effects.

Our observations demonstrate that the tetrapeptide H-Tyr-D-Arg-Phe-Gly-$NH_2$, possess significantly superior analgesic effects, compared to morphine. At the same time, unlike morphine H-Tyr-D-Arg-Phe-Gly-$NH_2$ does not cause toxic effects or psychological and behavioral disorders.

The result of our experiments is that we have produced a stable peptide that has an analgesic effect that is 10-times higher than that of morphine. An important consequence of our findings is that the preparation could be used in a wider therapeutic range that exceeds 200 therapeutic doses. This means that the drug does not represent a severe danger of an overdose, and can be safely used in various doses, depending on the severity of pain. Using the method of extrapolation, it was determined that the recommended dose for humans will range 0.01-10 mg/dose, and preferably 0.5-10 mg/dose, depending on the nature of pain.

The same results have been attained for preparations based on H-Tyr-D-Arg-Phe-Sar-OH.

Example 18

Clinical Applications

The use of the peptide compound in patients who have been informed about the drug and who have given their consent The peptide compound was used in cases where the patient has been prescribed an analgesic drugs of morphine group (3rd stage, according to the WHO system), but for one reason or another, the drug was not available. When the morphine drug therapy was once again possible, the use of the experimental prototype of the drug was stopped.

Based on the extrapolation of animal data for dosages for humans, we decided to use 0.7-3 mg of the active tetrapeptide in a single dose, administered by subcutaneous injection, and under the supervision of a specialist. The drug was packaged in lyophilized form of 3 mg per vial before use and dissolved in 1-3 ml of water for injections.

The following parameters were recorded:
1. Time of onset of analgesic effect, duration of effect. Dynamics of pain on a numerical scale of 0-10: 0—no pain, 10—unbearable pain. The patient makes regular notes on the intensity level of pain during treatment to assess the analgesic effect. Separately, the intensity of pain is noted before receiving the experimental prototype preparation, and during its' administration.
2. The physical activity of the patient.
Measured on a scale: 1—normal activity, 2—activity is reduced; the patient is able to go to their own doctor, 3—bed rest at least 50% of the day, 4—bed rest for more than 50% of the day, 5—complete bed rest.
3. Subjective feelings of the patient
A change of perception, mood, presence/absence of euphoria or dysphoria, discomfort in the body, feelings in the digestive tract.

Basically, the study was conducted in patients with somatic and internal types of pain, though often it was not possible to accurately classify the type of pain.

Patient 1. The patient is a 48 years old man.
Pancreatic cancer stage IV, metastasis. Pain on a scale of 6-9. Prescribe narcotic analgesics. The applied dose is to be 3 mg 2 times a day. Duration of therapy 5 days. Time of analgesia for 10-15 minutes. Subjective feelings: With the first injection, there was a very light dysphoric effect for 10-15 minutes, then the effect subsided. Disorder of consciousness or activity were not observed. Patient self-care. The degree of analgesia—on a scale of 1-3. The duration of analgesic effect—8-12 hours.

Patient 2. The patient is a 72 years old woman.
Colon cancer stage IV, metastasis. The pain does not stop, the patient screams in pain, cannot take care of herself and is not able to maintain normal conversation, and practically does not sleep. Applied dose of 2 mg three times during the first day, then reduced to 1.5 mg 2 times a day. Duration of therapy 4 days. Time of analgesia for 10-15 minutes. Subjective feelings: pain intensity was significantly reduced, recovered the ability to communicate, the patient was able to maintain a conversation, and was able to get up and walk normally, slept at night. No negative effects were detected. The degree of analgesia—on a scale of 2-3. The duration of analgesic effect—6-12 hours analgesic effect—6-12 hours.

Patient 3. The patient is a 56 years old woman.
Colon cancer stage IV, metastasis. Pain 7-10 scale. Prescribe narcotic analgesics. A dose of 1.5 mg is administered 2 times a day. Duration of therapy 4 days. Time of analgesia for 10-15 minutes. Subjective feelings: pain intensity was significantly reduced, the patient was able to maintain a conversation, and was able to get up and walk. No negative effects were detected. The degree of analgesia—on a scale of 1-3. The duration of analgesic effect—8-10 hours.

Patient 4. The patient is a 61 years old woman.
Breast cancer stage IV, metastasis. Pain 7-10 scale. Prescribed narcotic analgesics. The applied dose of 1.5 mg 2 times a day. Duration of therapy 5 days. The time of 10-20 minutes of analgesic effect. Subjective feelings: No feelings of euphoria or dysphoria, the intensity of pain was significantly reduced, and the patient was able to maintain a conversation. No negative effects were detected. The degree of analgesia—on a scale of 1-3. The duration of analgesic effect—8-10 hours.

Patient 5. The patient is a 53 years old woman.
Breast cancer stage IV, metastasis. Pain on a scale of 7-8. Prescribed narcotic analgesics. The applied dose is 0.7 mg two times a day 1.3, 1, 4.6 mg per day. Duration of therapy 6 days. Time of analgesia for 10-15 minutes. Subjective feelings: No feelings of euphoria or dysphoria, the intensity of pain was significantly reduced, the patient was able to maintain a conversation. No negative effects were detected. The degree of analgesia—on a scale of 1-3. The duration of analgesic effect—8-10 hours.

Patient 6. The patient is a 64 years old woman.
A compression fracture of a vertebra in the lumbar region. Pain on a scale of 7-8. Cannot move without assistance. A prescribed dose of 1.5 mg 2 times a day. The duration of therapy for 2 days. Time of analgesia for 10-15 minutes. Subjective feelings: No feelings of euphoria or dysphoria, the intensity of pain was significantly reduced, the patient was able to move to another city for further treatment. No negative effects were detected. The degree of analgesia—on a scale of 1-3. The duration of analgesic effect—8-12 hours.

Common in all of the cases above, it can be confirmed that there are no adverse reactions, such as impaired consciousness, euphoria or dysphoria, problems with the digestive tract, no any signs of respiratory depression or heart disorders. Patients that were administered the prototype drug could have normal communication with relatives.

Advantageously, in any compound, composition, pharmaceutical composition or medicament or analgesic peptide, or any preparation, method of treatment, method of administration, method of application or use of the same, of the present invention, either one or both of the following tetrapeptides can be used:

Tetrapeptide having an amino acid sequence H-Tyr-D-Arg-Phe-Gly-NH$_2$

Tetrapeptide having an amino acid sequence H-Tyr-D-Arg-Phe-Sar-OH

Whether either one of the tetrapeptides or a combination of both tetrapeptides listed above is used, the advantageous effects as specified in throughout the specification are achieved.

Those skilled in the art will appreciate that the invention described herein is susceptible to variations and modifications other than those specifically described. The invention includes all such variation and modifications. The invention also includes all of the steps, features, formulations and compounds referred to or indicated in the specification, individually or collectively and any and all combinations or any two or more of the steps or features.

Each document, reference, patent application or patent cited in this text is expressly incorporated herein in their entirety by reference, which means that it should be read and considered by the reader as part of this text. That the document, reference, patent application or patent cited in this text is not repeated in this text is merely for reasons of conciseness.

Any manufacturer's instructions, descriptions, product specifications, and product sheets for any products mentioned herein or in any document incorporated by reference herein, are hereby incorporated herein by reference, and may be employed in the practice of the invention.

The present invention is not to be limited in scope by any of the specific embodiments described herein. These embodiments are intended for the purpose of exemplification only. Functionally equivalent products, formulations and methods are clearly within the scope of the invention as described herein.

The invention described herein may include one or more range of values (eg. size, concentration, etc.).

A range of values will be understood to include all values within the range, including the values defining the range, and values adjacent to the range which lead to the same or substantially the same outcome as the values immediately adjacent to that value which defines the boundary to the range.

Throughout this specification, unless the context requires otherwise, the word "comprise" or variations such as "comprises" or "comprising", will be understood to imply the inclusion of a stated integer or group of integers but not the exclusion of any other integer or group of integers.

It is also noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Other definitions for selected terms used herein may be found within the detailed description of the invention and apply throughout. Unless otherwise defined, all other scientific and technical terms used herein have the same meaning as commonly understood to one of ordinary skill in the art to which the invention belongs.

LIST OF REFERENCES

1. Montecucchi P C et al.: Amino acid composition and sequence of dermorphin, a novel opiate-like peptide from the skin of *Phyllomedusa sauvagei*. Int J Pept Protein Res. 1981 March; 17(3):275-83.
2. Sasaki Y. et al.: The analgesic activity of D-Arg2-dermorphin and its N-terminal tetrapeptide analogs after subcutaneous administration in mice. Neuropeptides 1985; 5, Is. 4-6:391-394.
3. Chaki K. et al.: Comparison of the antinociceptive effects of new [D-Arg2]-dermorphin tetrapeptide analogs and morphine in mice. Pharmacol Biochem Behav. 1988 October; 31(2):439-44.
4. Chaki K. et al.: Antinociceptive cross-tolerance between [D-Arg2]-dermorphin tetrapeptide analogs and morphine. Peptides. 1990 January-February; 11(1):139-44.
5. Chaki K. et al.: Antinociception and physical dependence produced by [D-Arg2] dermorphin tetrapeptide analogues and morphine in rats. Br J Pharmacol. 1988 September; 95(1):15-22.
6. DeLean A. et al.: Simultaneous analysis of families of sigmoidal curves: application to bioassay, radioligand assay, and physiological dose-response curves. Am J Physiol. 1978 August; 235(2):E97-102.
7. Susan J. et al. Opiate-induced Analgesia is increased and prolonged in mice lacking P-glycoprotein. Anesthesiology, 2000, V. 92, P. 1392-9.

The invention claimed is:

1. A composition for injections and/or nasal administration for preventing and/or treating acute and/or chronic pain; said composition comprising:
   a therapeutically efficacious quantity of a tetrapeptide, as an active ingredient, said tetrapeptide having an amino acid sequence H-Tyr-D-Arg-Phe-Gly-NH2 or H-Tyr-D-Arg-Phe-Sar-OH, and
   at least one excipient, with the following component ratios, weight %:
   the tetrapeptide: 0.01-0.5, and
   said at least one excipient: up to 100.

2. The composition according to claim 1, wherein said at least one excipient is selected from the group consisting of: a stabilizer, a release modifier, a buffering additive, an emulsifier/solubiliser, a solvent, a filler, and a preservative.

3. The composition according to claim 2, wherein the stabilizer further includes at least one substance selected from the group consisting of: Trilon B, sodium metabisulfite, sodium thiosulfate, glycine, arginine, histidine, lysine, glycine hydrochloride, glycine maleate, arginine hydrochloride, arginine acetate, arginine glutamate, arginine maleate, histidine hydrochloride, histidine acetate, lysine hydrochloride, lysine sulphate, and lysine maleate.

4. The composition according to claim 2, wherein the release modifier further includes at least one substance selected from the group consisting of: polyvinylpyrrolidone with a molecular weight of 10-60 kDa, dextran with a molecular weight of 10-100 kDa, polyvinyl alcohol, and sodium carboxymethylcellulose.

5. The composition according to claim 2, wherein the buffering additive further includes at least one substance selected from the group consisting of: sodium chloride, sodium/potassium hydrogen, dihydrogen phosphate, sodium, and ammonium acetate.

6. The composition according to claim 2, wherein the emulsifier/solubiliser further includes at least one substance selected from the group consisting of: soy lecithin for injections, polysorbate 20, polysorbate 60, polysorbate 80, Span 20, Span 40, Span 60, Span 85, and sodium dodecyl sulphate.

7. The composition according to claim 2, wherein the solvent further includes at least one substance selected from the group consisting of: water for injections, sterile saline solution, olive oil, peach kernel oil, and sunflower oil.

8. The composition according to claim 2, wherein the filler further includes at least one substance selected from the group consisting of: sorbitol, mannitol, mannitol, xylitol, lactose, sucrose, dextrose, and poly lactic-co-glycolic acid.

9. The composition according to claim 2, wherein the preservative further includes at least one substance selected from the group consisting of: chlorobutanol hydrate, ethyl alcohol, benzyl alcohol, phenol, meta-cresol, chloro-cresol, benzoic acid, sorbic acid, merthiolate, Nipagin, Nipasol, benzalkonium chloride or bromide, benzethonium chloride, cetylpyridinium chloride, dimethyldodecylbenzylammonium chloride, methylparaben, and propylparaben.

10. The composition according to claim 1, wherein the composition is provided in a form selected from the group consisting of:
   a powder form;
   a liquid dosage form for administration for intramuscular or intravenous injection, subcutaneous or intradermal injection;
   a liquid form for infusion administration; and
   a liquid form for nasal administration.

11. The composition according to claim 10, wherein the composition is provided in:
   the liquid dosage form for administration for intramuscular or intravenous injection, subcutaneous or intradermal injection; or
   the liquid form for infusion administration; or
   the liquid form for nasal administration, and
   the composition has a pH of from 4 to 8.

12. The composition according to claim 11, wherein the composition has a pH of from 4.5 to 5.5.

13. The composition according to claim 10, wherein an injectable dosage is provided in the liquid dosage form; said injectable dosage consists of a number of components as follows, in weight %:

| | |
|---|---|
| buffer: | 0.01-0.2, |
| filler: | 0-6, |
| stabilizer: | 0-4, |
| the tetrapeptide: | 0.01-0.5, and |
| solvent: | up to 100. |

14. The composition according to claim 13, wherein the components of the injectable dosage are represented by the following substances, in weight %:

| | |
|---|---|
| the buffer is sodium acetate: | 0.04; |
| the filler is mannitol: | 0.5; |
| the stabilizer is represented by: | sodium chloride-0.5, and glycine-0.5; |
| the tetrapeptide is peptide: | 0.15; |
| the solvent is water for injections: | up to 100; and |
| the composition has a pH up to | 4.7. |

15. The composition according to claim 10, wherein the composition is provided in the powder form; said composition is further diluted with solvent to a dosage of 1 mL, said dosage consists of a number of components as follows, in mg/mL weight:

| | |
|---|---|
| buffer: | 0.01-0.2, |
| filler: | 0-6, |
| release modifier: | 0-8, |
| stabilizer: | 0-4, and |
| the tetrapeptide: | 0.01-0.5. |

16. The composition according to claim 15, wherein the following components selected from said number of components are represented by the following substances, in mg/mL:

| | |
|---|---|
| the buffer is sodium acetate: | 0.4 mg; |
| the filler is mannitol: | 5 mg; |
| the stabilizer is glycine: | 5 mg; |
| the tetrapeptide: | 1.5 mg; and |
| the composition has a pH up to | 4.7. |

17. The composition according to claim 10, wherein the composition is provided in a dosage of said liquid form for nasal administration, said dosage consists of a number of components as follows, in weight %:

| | |
|---|---|
| buffer: | 0.01-0.2, |
| filler: | 0-1.5, |
| stabilizer: | 0-1.5, |
| the tetrapeptide: | 0.01-0.5, |
| preservative: | 0-0.5, and |
| solvent: | up to 100. |

18. The composition according to claim 17, wherein the components of the dosage are represented by the following substances, in weight %:

| | |
|---|---|
| the buffer is sodium acetate: | 0.04, |
| the filler is mannitol: | 0.5, |
| the stabilizer is represented by: | glycine-0.5 and sodium chloride-0.5, |
| the tetrapeptide: | 0.15, |
| the preservative is meta-cresol: | 0.1, |
| the solvent is water for injections: | up to 100; and |
| the composition has a pH up to | 4.7. |

* * * * *